(12) United States Patent
Stromberg (10) Patent No.: US 7,044,930 B2
(45) Date of Patent: May 16, 2006

(54) MULTI-MODULAR ARRANGEMENT FOR ANAESTHESIA

(75) Inventor: Stefan Per Axel Stromberg, Sigtuna (SE)

(73) Assignee: Aneo AB, Marsta (SE)

( * ) Notice: Subject to any disclaimer, the term of this patent is extended or adjusted under 35 U.S.C. 154(b) by 74 days.

(21) Appl. No.: 10/181,491

(22) PCT Filed: Jan. 24, 2001

(86) PCT No.: PCT/SE01/00130

§ 371 (c)(1),
(2), (4) Date: Jul. 19, 2002

(87) PCT Pub. No.: WO01/54751

PCT Pub. Date: Aug. 2, 2001

(65) Prior Publication Data

US 2002/0189609 A1   Dec. 19, 2002

(30) Foreign Application Priority Data

Jan. 25, 2000   (SE) .................................. 0000229

(51) Int. Cl.
*A61M 31/00* (2006.01)

(52) U.S. Cl. .......................................... 604/65; 604/67

(58) Field of Classification Search ................ 604/65, 604/66, 67, 30, 31; 600/26; 439/296, 297; 361/600
See application file for complete search history.

(56) References Cited

U.S. PATENT DOCUMENTS

| | | | | |
|---|---|---|---|---|
| 3,014,160 A * | 12/1961 | Brogden | ...................... | 361/727 |
| 4,151,580 A * | 4/1979 | Struger et al. | .............. | 361/801 |
| 4,716,495 A * | 12/1987 | Craker | ........................ | 361/725 |
| 4,738,632 A * | 4/1988 | Schmidt et al. | .............. | 439/341 |
| 4,858,101 A * | 8/1989 | Stewart et al. | .................. | 700/2 |
| 5,339,362 A * | 8/1994 | Harris | ........................ | 381/86 |
| 5,352,195 A * | 10/1994 | McEwen | ...................... | 604/66 |
| 5,522,042 A * | 5/1996 | Fee et al. | .................... | 709/226 |
| 5,547,470 A * | 8/1996 | Johnson et al. | ................ | 604/67 |
| 5,564,059 A * | 10/1996 | Maskovyak et al. | ........... | 707/6 |
| 5,601,445 A * | 2/1997 | Schipper et al. | ............ | 439/341 |
| 5,713,856 A * | 2/1998 | Eggers et al. | ................. | 604/65 |
| 5,761,033 A * | 6/1998 | Wilhelm | ...................... | 361/686 |
| 5,781,745 A * | 7/1998 | Ramelson et al. | .......... | 710/113 |
| 5,957,885 A * | 9/1999 | Bollish et al. | ................. | 604/67 |
| 6,362,951 B1 * | 3/2002 | Moribe et al. | .............. | 361/600 |
| 6,790,178 B1 * | 9/2004 | Mault et al. | ................. | 600/300 |

* cited by examiner

*Primary Examiner*—Aaron J. Lewis
(74) *Attorney, Agent, or Firm*—Banner & Witcoff, Ltd.

(57) ABSTRACT

The invention relates to an arrangement for inducing a state of anaesthesia in a living creature and maintaining the creature in that state by administering to the said creature an infused volume of liquid anaesthesia-inducing medication per unit of time, preferably during the use of one or more lung ventilation unit(s)s and one or more infusion unit(s).

The arrangement comprises a basic unit (102) with control function software (600*a'*–600*r'*) and one or more modular unit(s) (30', 30, 30") containing hardware for the control functions. When a modular unit (30') co-acts with the basic unit (102), it (30') activates the control functions stored in the basic unit (102).

29 Claims, 3 Drawing Sheets

MULTI-MODULAR ARRANGEMENT FOR ANAESTHESIA

This is a U.S. National Phase Application Under 35 USC 371 and applicant herewith claims the benefit of priority of PCT/SE01/00130 filed Jan. 24, 2001, which was published Under PCT Article 21(2) in English, and Sweden Application No. 0000229-5 filed Jan. 25, 2000.

FIELD OF INVENTION

The present invention relates to an arrangement for initially inducing a state of anaesthesia in a living creature and maintaining the creature within suitable limits for the said state of anaesthesia, i.e. an appropriate depth of anaesthesia.

These states and depths of anaesthesia can be achieved e.g. by supplying the living creature with an infused or injected volume of a liquid anaesthesia inducing drug per unit of time.

The term 'infused' refers to continuous or intermittent and/or adjustable administration, often intravenous, of the said drug (anaesthetic) into a blood vessel of the living creature.

The objective of the present invention is to achieve a procedure in every application for inducing a state of anaesthesia in a creature, although not in any application related to inhalation anaesthesia in which the anaesthesia-inducing drug is carried through the airways into the lungs with a volume of air during an insufflation phase and in which part of the anaesthesia-inducing drug accompanies the air during an expiratory phase.

For the sake of simplification, the following description will only use "intravenous" anaesthesia as a collective designation for all the forms of anaesthesia within the scope of the present invention.

The use of e.g. a lung ventilator with an associated control unit and an infusion unit or the equivalent with an associated control unit are often required during the induction of anaesthesia in order regulate the need, i.e. increase or decrease, the volume of drug administered per unit of time in maintaining a depth of anaesthesia.

Arrangement of this kind comprise and/or also include a plurality of sensors and or measurement probes devised to sense selected creature criteria and emit signals corresponding to a selected criterion's momentary value or intensity.

A number of examples of selected criteria and their intensity will be provided hereinafter.

The invention is applicable to any living creature with a pulmonary function and shall be illustrated below, for the sake of simplicity, as applied to a human being, represented by a patient undergoing surgery.

PRIOR ART

As regards previously known arrangements and devices, devised for limited application to the present invention, for inducing a state of anaesthesia and a selected depth of anaesthesia in a patient, dividing such states into three different categories is common, depending on the patient's degree of consciousness, viz.

General anaesthesia, in which the patient is in a state of artificial unconsciousness and is kept with appropriate degrees or levels of unconsciousness (depth of anaesthesia).

Regional anaesthesia, in the form of spinal anaesthesia, and

Local anaesthesia, mainly used for minor procedures.

The patient is in a conscious state in the last two categories.

The present invention is therefore devised for application in all the aforementioned categories.

The "general anaesthesia" category encompasses two different groups, viz. a group in which the present invention is not intended for use and which is referred to as 'inhalation anaesthesia' and a group in which the present invention has application and which is referred to, for the sake of simplicity', as 'total intravenous anaesthesia' or intravenous anaesthesia.

A lung ventilator with vaporiser equipment for an anaesthesia-inducing drug is employed in the inhalation anaesthesia group. The lung ventilator creates conditions for insufflation and expiration of air or air mixed with oxygen which is mixed, in turn, with anaesthesia-inducing gases.

Devices for inhalation anaesthesia are in widespread use but require highly complex equipment for controlling insufflation and expiration phases, for administering the delivery of gaseous drug and, additionally, evaluating patient-related criteria when necessary.

In this application, expired gas contains anaesthesia-inducing gases in every expiratory phase, so these gases must be evacuated from every enclosed space, such as an operating theatre. The equipment must also be gas-tight.

Creating inhalation anaesthesia-related systems in different department by arraying different devices from different manufacturers and designed for different purposes is previously known for this application.

Utilising a single system from one manufacturer is also known. However, any such system is highly complex, and its components make the equipment very heavy. The system has also been found to be bulky and expensive and requisite leakage tracing is far more difficult.

The objective of the present invention is to achieve an especially suitable application for the second group, i.e. the general anaesthesia category, referred to as intravenous anaesthesia involving the infusion of a volume of a liquid anaesthesia-inducing drug per unit of time into a blood vessel of the living creature or patient.

In this application, it is common to utilise a lung ventilator and an infusion unit, the latter, a control unit enabling the latter to induce a depth of anaesthesia and maintain the patient within appropriate limits for the selected depth of anaesthesia.

Utilising a plurality of devices from different manufacturers and arraying them into a system or an arrangement is also previously known.

Each such arrangement for inducing a depth of anaesthesia in a patient demands the use of a plurality of devices and measurement apparatuses for evaluating, with their help, a plurality of important criteria for the patient and for controlling the patient's well-being. As a rule, these criteria are displayed as momentary values and/or curves on each device's display screen.

Criteria related to the patient's well-being/treatment are referred to as 'therapeutic criteria', and they are sensed, regulated and evaluated by one or more therapeutic unit(s).

Criteria related to the patient's diagnosis or monitoring are referred to as 'diagnostic criteria', and they are sensed and evaluated in one or more diagnostic unit(s).

Some currently important units and criteria are listed in FIG. 1 of the Swedish patent application 99 01688-3.

Since the present invention can advantageously be used in an arrangement of the kind described therein, the contents of the said patent application shall be regarded as a part of this application, and the following description will make direct reference to the said patent application.

DESCRIPTION OF THE INVENTION

Technical Problems

When taking into consideration the technical deliberations that a person skilled in this particular art must make in order to provide a solution to one or more technical problem(s) that she/he encounters, it will be seen that, on the one hand, it is initially necessary to realize the measures and/or sequence of measures that must be undertaken to this end and, on the other hand, to realize which means is/are required to solve one or more of said problem(s). On this basis, it will be evident that the technical problems listed below are relevant to achieving the present invention.

With a view to the prior art, as described above, a technical problem will be seen to reside in devising with simple means an arrangement, adaptable to one or more application(s), for inducing a state of anaesthesia in local areas of the body of a living creature or in the entire body of the living creature and maintaining the creature in this state by administering to the said creature a regulated amount and/or volume of anaesthesia-inducing medication per unit of time, only using intravenous anaesthesia according to the aforementioned definition.

A technical problem will also be seen to reside in being able to realize the importance of and advantages associated with easy attachment and removal of one ore more modular unit(s) to/from the basic unit. Selected modular units, when co-acting with the basic unit, shall be devised to activate one or more function(s), primarily stored as software in the basic unit. Selected modular units shall also be devised to measure or monitor the creature's diagnostic criteria and/or control the creature's therapeutic criteria.

A technical problem will also be seen to reside in being able to *ealiee realize the importance of and advantages associated with devising selected modular units to incorporate units capable of sensing diagnostic criteria, or devising selected modular units to incorporate units capable of affecting therapeutic criteria.

A technical problem will also be seen to reside in being able to realize the importance of and advantages associated with having the said modular units, devised to incorporate units capable of sensing diagnostic criteria, even incorporate one or more computer unit(s) with associated software or having the said selected modular units, devised to incorporate units capable of affecting therapeutic criteria, even incorporate one or more computer unit(s) with associated software.

A technical problem will also be seen to reside in being able to realize the importance of and advantages associated with implementing selected basic unit functions by means of co-action of the basic unit and one or more modular unit(s). Necessary software can be in the basic unit and in one or more modular unit(s), depending on the function selected for the utilised units.

A technical problem will additionally be seen to reside in being able to realize the importance of and advantages associated with incorporating, in whole or part, requisite function-related hardware in a modular unit and incorporating, in whole or part, function-related software in the basic unit.

A technical problem will also be seen to reside in being able to realize the importance of and advantages associated with incorporating e.g. a system-identifying circuit with a selected electronic interface, a contact and function-related sensors or the like in each modular unit.

A technical problem will also be seen to reside in being able to realize the importance of and advantages associated with incorporating e.g. a module-identifying and/or function-identifying circuit, devised to activate relevant software stored in the basic unit, in the respective modular unit.

A technical problem will also be seen to reside in being able to realize the importance of and advantages associated with having the said function-related software in the basic unit be updateable, with or without a modular unit co-acting with the said basic unit.

A technical problem will also be seen to reside in being able to realize the importance of and advantages associated with devising a selected modular unit with specific hardware and/or software for a single function.

A technical problem will also be seen to reside in being able to realize the importance of and advantages associated with devising a selected modular unit with specific hardware and/or software for a plurality of selected functions.

A technical problem will also be seen to reside in being able to realize the importance of and advantages associated with devising a selected plurality of modular units with specific hardware and/or software for a single function.

A technical problem will also be seen to reside in being able to realize the importance of and advantages associated with having one or more selected modular unit(s), co-acting with the said basic unit, provide sensing of and/or processing and/or control of one or more function-related criterion/criteria.

A technical problem will also be seen to reside in creating conditions, using simple coordinated measures, for simple replacement of one form of anaesthetic with another during ongoing surgery, e.g. by the addition of or replacement of one utilised module with another modular unit, or combination of modular units, which satisfy the new requirements.

A technical problem will additionally be seen to reside in creating conditions, using simple means, in which selected forms of anaesthesia (such as intravenous) can be induced in operating theatres with access to a basic unit, activatable by one or more of the invention's modular unit(s).

A technical problem will additionally be seen to reside in creating conditions in which a user only needs to tie up capital to meet a prevailing need, i.e. in a basic unit and a selected number of modular units. Additions can be simply made to accommodate other e.g. more complex needs by procuring the corresponding modules.

A technical problem will moreover be seen to reside in being able to realize the importance of and advantages associated with utilisation of a basic unit computer unit which can be activated and upgraded in a quality-assured fashion, more or less regardless of the configuration of available modular units.

A technical problem will additionally be seen to reside in providing a software interface for this application by means of a touch screen (no buttons/knobs on the basic unit or modular unit) and providing simple updating of the system's language function and even increased opportunity for remote control.

A technical problem will also be seen to reside in being able to realize the importance of and advantages associated with utilisation of a modular unit which automatically updates a user interface when mounted for co-action with the basic unit.

A technical problem will also be seen to reside in creating conditions, using simple means, for a long operating life for the basic unit by requisite adaptation to new developments by adding one or more modular unit(s) and by upgrading basic unit software.

A technical problem will be seen to reside in creating conditions, using simple means, in which the same system with user interfaces can be used by all operating theatres in a given area for selected forms of anaesthesia, thereby simplifying handling and increasing patient safety.

A technical problem will additionally be seen to reside in being able to realize the importance of and advantages associated with controlling a first means and/or a second means with the aid of one or more computer unit(s) and activating selected functions with a modular unit.

A technical problem will additionally be seen to reside in being able to realize the importance of and advantages associated with devising the said basic unit-related computer unit so it is able to make a distinction between therapeutic criteria and diagnostic criteria by means of therapeutic units and/or diagnostic units incorporated into modular units.

A technical problem will additionally be seen to reside in being able to realize the importance of and advantages associated with structuring one or more therapeutic unit(s) and/or one or more diagnostic unit(s) on a board with printed circuitry and, where applicable, mounted on or related to functional units. A plurality of the said boards is arrayed in the modular unit. An input connector and/or an output connector for each modular unit consists of one part of a two-part connection means, and the other part is on the basic unit.

A technical problem will also be seen to reside in creating conditions, using simple means, in which a display unit, devised to display momentary values for one or more criterion/criteria and or the criteria's chronological variation, can be connected to and/or easily detached from the basic unit.

A technical problem will therefore be seen to reside in being able to realize the importance of and advantages associated with co-ordinated presentation of requisite diagnostic criteria and requisite therapeutic criteria, thereby greatly facilitating the anaesthesiologist's and surgeon's monitoring and regulation of the patient's therapeutic criteria and/or diagnostic criteria, such as the depth of anaesthesia and/or other changeable conditions.

A technical problem will also be seen to reside in creating conditions, using simple means, for presentation on a monitor or display of the chronological variation of a selected number of criteria with at least several selected, co-ordinated time axes, e.g. stacked atop one another, and with compensation, when required, for any lag time needed in evaluating certain measurement results.

A technical problem will also be seen to reside in using a display unit, devised for incorporation in an arrangement and co-acting with a basic unit, for presenting chronological variations in measurement values for the selected criteria and momentary values for the same or other selected criteria and structuring these values on the display so they are easily legible. The said display can then present one or more criterion/criteria for a patient with a selected depth of anaesthesia induced when the said creature was administered and infusion of a volume of anaesthesia-inducing drug.

A technical problem will also be seen to reside in distributing, in a simple fashion, measurement values received and information on selected patient-related criteria so they are readily legible on the screen and easily adjustable, e.g. through the use of display fields, the positioning of these fields on the screen and/or the action of a button or knob.

A technical problem will also be seen to reside in being able to realize the importance of devising a first large area in the said display for presenting chronological variation in a number of criteria and a second, smaller area in the said display for presenting the momentary values for a number of criteria, maximum values, minimum values etc.

A technical problem will also be seen to reside in being able to realize the importance of and advantages associated with devising the first display area to display the chronological variation in a number of criteria by positioning a selected number of them with identical time axes stacked atop one another.

A technical problem will also be seen to reside in being able to realize the importance of and advantages associated with dividing the a second display area into fields, each field designating current criteria, e.g. in. abbreviated form, and additionally designating the criteria's momentary values, maximum or minimum values or calculated values.

A technical problem will further be seen to reside in being able to realize the importance of and advantages associated with having a rotating, easily detached display unit on the front of the basic unit, as over an opening for a plurality of modular units, in an arrangement of the initially described kind with a basic unit and a display unit.

A technical problem will additionally be seen to reside in creating an arrangement, using simple means, for total intravenous anaesthesia in which the arrangement is far easier to use previously known coordinated arrangement arrays, devised to meet official demands. This will lead to reduced maintenance costs, greater operating reliability, smaller space requirements, greater associated mobility and simpler, more cost-effective upgrades to meet future demands and/or wishes.

Solution

The present invention accordingly takes as its starting point an arrangement for inducing a state of anaesthesia in a living creature and maintaining that creature in this state by administering a regulated amount and/or volume of anaesthesia-inducing medication per unit of time according to a previously stated definition.

With the intention of solving one or more of the aforesaid technical problem(s), it is proposed that one or more modular unit(s) is/are easily attached to and detachable from a basic unit. The selected modular units, when co-acting with the basic unit, shall be devised to activate one or more function(s), primarily stored as software in the basic unit. Selected modular units are also devised to measure or monitor the creature's diagnostic criteria and/or control the creature's therapeutic criteria.

According to proposed embodiments that lie within the scope of the present invention, it is proposed that selected modular units be devised to incorporate diagnostic criteria-sensing units or that selected modular units be devised to incorporate units capable of affecting therapeutic criteria.

It is further proposed that the said modular units, devised to incorporate diagnostic criteria-sensing units, can also incorporate one or more computer unit(s) with software or that the said selected modular units, devised to incorporate units capable of affecting therapeutic, can also comprise one or more computer unit(s) with software.

Selected basic unit function can be achieved by co-action of the basic unit and one or more modular unit(s). The requisite software can be distributed between the basic unit and one or more modular unit(s), depending on the modular units employed.

It is further proposed that function-related hardware, related to one or more criterion/criteria, be incorporated into a modular unit and/or function-related software for one or more modular unit criterion/criteria be incorporated into the basic unit.

It is further proposed that each modular unit shall incorporate e.g. a system-identifying circuit with a selected electronic interface, a contact and function-related sensors or the like.

It is further proposed that the respective modular unit can contain e.g. a module-identifying and/or a function-identifying circuit devised to activate selected software stored in the basic unit.

It is further proposed that the said function-related software can be updateable with or without the basic unit modular unit co-acting with the said basic unit.

A modular unit can be devised with hardware and/or software for a single function.

A modular unit can be devised with hardware and/or software for a plurality of selected functions.

Alternately a selected number of modular units can be devised with hardware and/or software for a single function.

One or more selected modular unit(s), co-acting with the said basic unit, shall be able to provide sensing of and/or processing of and/or control of one or more function-related criterion/criteria.

The said criteria can therefore be related to one or more modular unit(s).

As examples hereof, it is proposed that one of more modular units be devised for:
a) Oxygen measurement employing paramagnetic sensing.
b) Oxygen measurement employing chemical cells.
c) Carbon dioxide measurement.
d) Pulse oximetry.
e) ECG.
f) Bi-spectral index.
g) Pressure, flow and/or volume in one unit.
h) NIBP value (blood pressure measured with a cuff).
i) IBP (blood pressure measured with a cannula in a blood vessel).
j) Measurement of (patient) temperature.
k) Cardiac output (measurement of the heart's minute volume).
l) Lung ventilator, simple type.
m) Lung ventilator, advanced type.
n) Lung ventilator, high-frequency type.
o) Blood occlusion regulator.
p) Oxygen administration.
q) Infusion units of various kinds.
r) Nitrous oxide administration.

It is further proposed that devising an individual modular unit which activates and/or controls computer-related or basic unit-related functions, as listed under a, b, c and d above, shall be possible.

Alternately, a modular unit can be devised for functions under e and h, under l, m or n, preferably l and g, under m and g, under l, k and j and/or under p and b or under p and a. It is further proposed that the said computer unit can be devised to distinguish between therapeutic criteria and diagnostic criteria by means of therapeutic units and/or diagnostic units in modular units.

It is further proposed that one or more therapeutic unit(s) and/or one or more diagnostic unit(s) be arrayed on a single board with printed circuitry and, where applicable, mounted on functional units. A plurality of the said boards are arrayed in the modular unit. An input connector and/or an output connector for each modular unit is connected as a first part of a two-part connection means for the basic unit.

In order to solve one or more of the aforesaid problem(s), it is further proposed that one or more first criterion/criteria, related to one or more modular unit(s) containing one or more diagnostic unit(s), and one or more other criterion/criteria, related to one or more modular unit(s) containing one or more therapeutic unit(s), can be displayed on a screen. One or more of the said first criterion/criteria is/are selected for display on the screen as momentary values, and criterion/of the said first criteria is/are selected for display on the screen as the criterion's/criteria's chronological variation.

As proposed embodiments within the scope of the present invention, it is further proposed that one or more of the said other criterion/criteria be selected for display on the screen as momentary values and that one or more of the said other criterion/criteria be selected for display on the screen as the criterion's/criteria's chronological variation.

The time axes for certain criteria, selected for display as the criterion's chronological variation, can be co-ordinated and stacked atop one another.

Sensor signals for a plurality of criteria may need to be delayed in order to suit time-delayed signals.

It is further proposed that momentary values for one or more criterion/criteria, related to one or more diagnostic unit(s) and/or momentary value(s) for one or more criterion/criteria related to one more therapeutic unit(s) be storable in memories for presentation, when needed, as the criterion's chronological variation.

The opportunity is also provided for time-related storage in memory of a number of selected momentary values for presented chronological curves so the trend of curve progression or variation in a chronologically compressed form can be re-displayed.

Advantages

The main advantages which can be regarded as significant for an arrangement for inducing a state of anaesthesia in a living creature or a patient are that the invention creates conditions for functional co-ordination of requisite circuits, although primarily computer software, for certain applications in a single unit which is easy to transport and takes up little space. In this manner, basic unit control functions can be activated by one or more separate modular unit(s), easily attached to and removed from the said basic unit.

A selected modular unit can accordingly be devised for measuring or monitoring and/or controlling, via the basic unit computer unit, one or more selected criterion/criteria-related functions from a much larger number of functions accessible and stored in the basic unit.

The features deemed to be characteristic of an arrangement according to the present invention are set forth in the characterising clause of claim 1 below.

BRIEF DESCRIPTION OF THE FIGURES

An arrangement currently proposed for inducing a state of anaesthesia in a living creature or a patient will now be exemplifyingly described, referring to the attached drawings in which.

DESCRIPTION OF THE PROPOSED EMBODIMENT

Since the present invention is intended for advantageous use in an arrangement for inducing an intravenous state of anaesthesia in a living creature and since such an arrangement is illustrated and described in Swedish patent application no. 99 01688-3, the contents of this patent application shall be regarded as part of this description.

The said patent application shows that an equipment unit or a basic unit 102 is equipped with a computer unit 600 with requisite software for a number of functions and/or criteria and a number of memories required for this.

The said computer unit 600 is devised to co-act with a number of control means for sensing, calculating and/or controlling various criteria-related functions in the arrangement.

To put it simply, a computer-controlled control means is conceivable with software and a memory for each function in which a selected number from a number of available functions are listed in the following.

Figure 1:
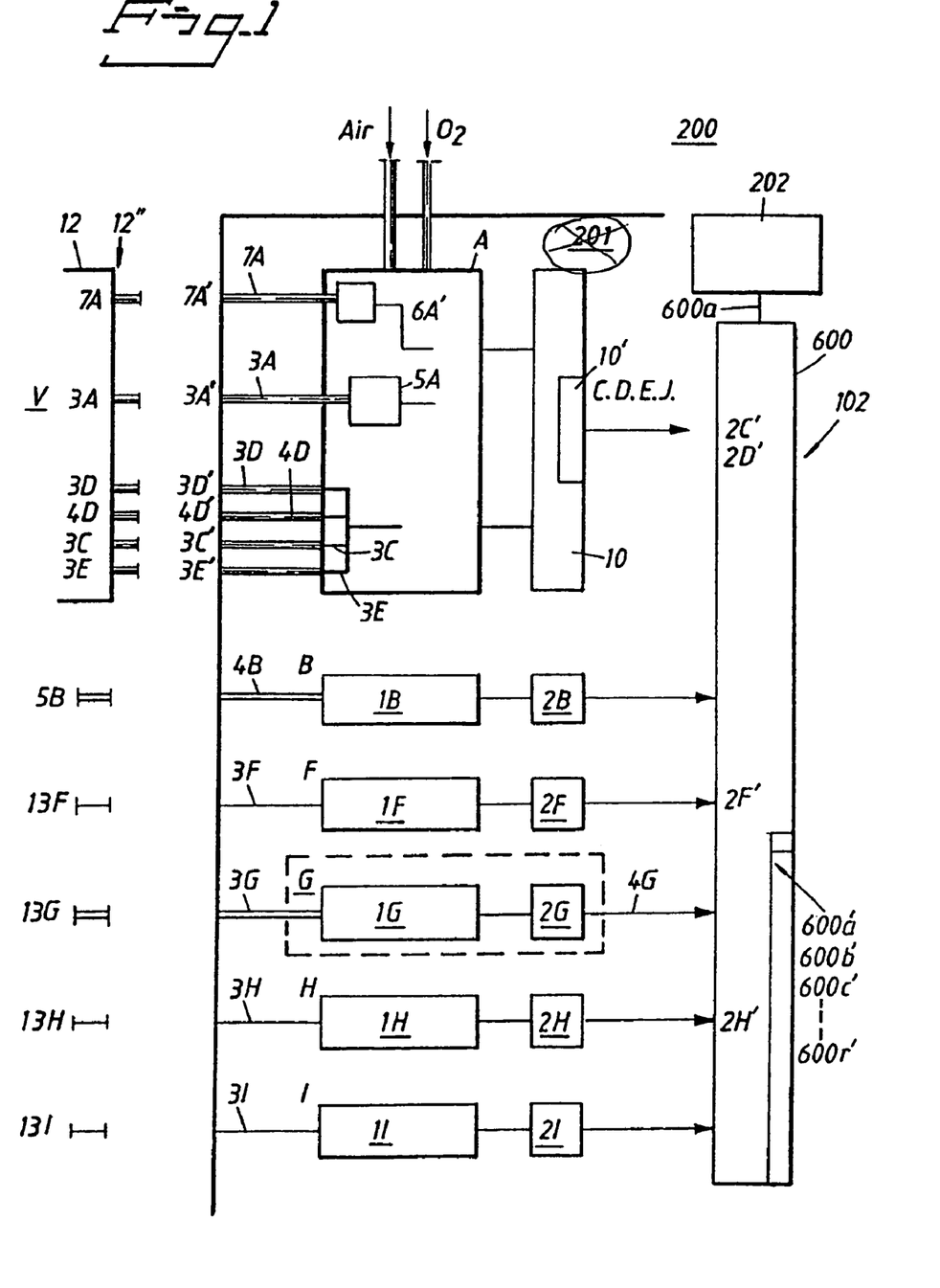
FIG. 1 depicts the principle of the present invention with a reference to FIG. 3 in the aforesaid patent application.

Thus, the computer 600 in FIG. 1 will be able to comprise a large number of computer-controlled, software-related control means and functional blocks with associated memories, even if the functions for most of these control means could be coordinated with software.

This co-ordination particularly applies to a first means in a first category in which the patient's well-being/treatment are taken into account and a second category in which the patient's diagnosis or monitoring are taken into account.

The invention is based on the circumstance that each criteria-related function 600a'–600r', regardless of whether it is related to therapy or diagnosis, is performed by co-action of one or more modular unit(s) and the basic unit.

A subdivision shall be made between one or more computer-controlled control means, with associated basic unit memories, so the basic unit part contains control functions, and a second modular unit part contains activation and initiation functions.

The basic unit part for the selected criteria and associated functions has been assigned the reference designations 600a'–600r' in which "a" to "r" represent the subsequently stipulated criteria.

These functions are mainly represented with software in a basic unit 102 which is part of the computer unit 600.

According to the invention, the functions 600a'–600r' shall be dependent on and related to selected modular units.

One unit or a module G in FIG. 1 can be cited as a first example.

This unit G shall contain a blood pressure-evaluating unit with a sensor unit 1G and an evaluating or calculating unit 2G for evaluating the NIBP value.

According to the invention, at least the sensing unit 1G shall be part of a separate modular unit G, but there is nothing to prevent incorporating even the evaluating unit 2G which would otherwise be in the computer 600.

A tube 13G and 3G from the patient V is connected to this modular unit G, and the modular unit G is electrically connected via a line 4G and connection means to the basic unit computer 600.

Control functions for all criteria 600a'–600r' shall primarily be co-ordinated by the basic unit 102, whereas activation and initiation functions will be provided outside the basic unit 102 in one or more of the utilised modular unit(s), such as modular unit G.

Obviously some co-ordination of a number of activation and initiation function will be able to take place in a single modular unit.

More especially, the present invention proposes that the first means and/or second means shall be activatable and controllable with the aid of stored software but that selected criteria-related functions, related to the said first and/or second means, shall be activatable via hardware and possibly software included in a separate modular unit, such as modular unit G.

Figure 4:
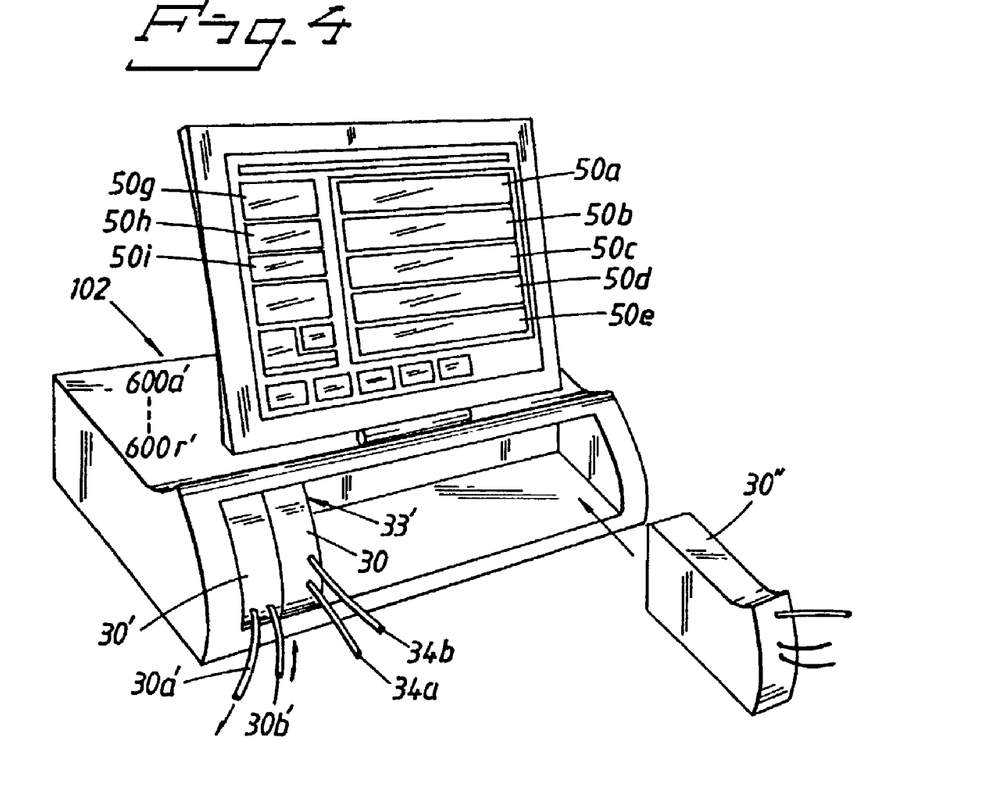
FIG. 4 shows a perspective view of a basic unit with a recess, for admitting a number of external modular units, and in which a display shows a first embodiment with two selected modular units.

As a unit, the said modular unit G is easily attached to and removed from the said basic unit, as FIG. 4 shows. The respective modular unit be insertable into or withdrawable from the basic unit 102.

The modular units for A, B, F, H and I can be devised in the corresponding fashion with a tube or electric line between the patient and the modular unit, the modular unit electrically co-acting with the basic unit.

The said modular unit is therefore devised for controlling a selected number of computer unit functions and basic unit functions from a large number of functions available therein.

The invention is therefore based on an arrangement for inducing a state of anaesthesia in a living creature and maintaining the creature in this state by the administration of a regulated amount and/or volume of anaesthesia-inducing medication per unit of time. It is only applicable to intravenous anaesthesia according to the definition provided above.

It is further proposed that one or more modular unit(s) (G and/or 30), 30 and 30" respectively, shall be easily detachable to and easily removable from a basic unit 102.

Selected modular units are devised to measure and, when co-acting with the basic unit, activate the criteria-related functions 600a'–600r', stored primarily as software, in the basic unit.

Selected modules are devised to monitor the creature's diagnostic criteria and/or control the creature's therapeutic criteria.

Selected modular units can, thus, be devised to include units for sensing diagnostic criteria, or selected modules can be devised to include units capable of affecting therapeutic criteria.

The said modular units, devised to include units for sensing diagnostic criteria, can also include one or more computer unit(s) with associated software.

The said selected modular units, devised to include units capable of affecting therapeutic criteria, can also include one or more computer unit(s) with associated software.

Thus, the selected basic unit functions 600a'–600r' will be achievable through co-action of the basic unit 102 and one or more modular unit(s), and the requisite software can be divided between the basic unit and one or more modular unit(s), depending on the modular units employed.

Function-related hardware for one or more criterion/criteria shall primarily be arranged in one modular unit.

Function-related software for one or more criterion/criteria are arranged in the basic unit 102.

Figure 3:
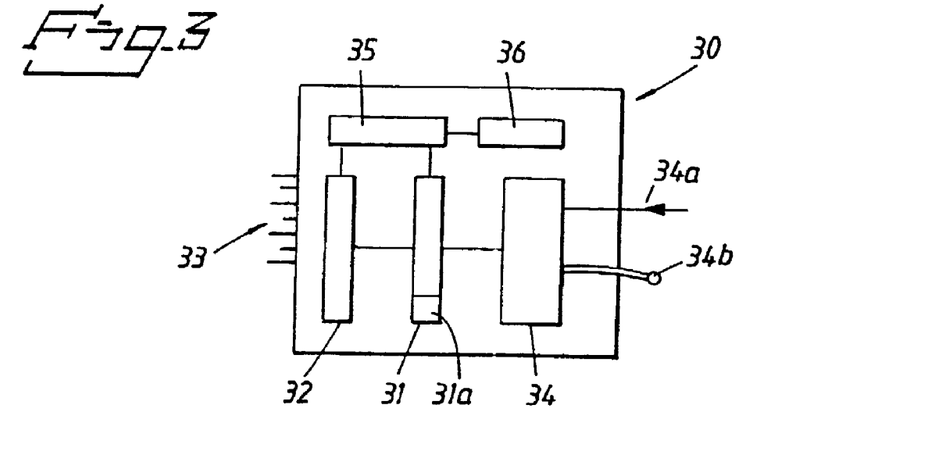
FIG. 3 is a block diagram of the principle for devising a modular unit with a plurality of functions.

FIG. 3 shows that a modular unit 30 should include e.g. a system identification circuit 31 with a selected electronic interface 32, a contact 33 and function-related sensors 34 or the like. Here, the sensor 34 is devised for e.g. oxygen measurement.

The sensor 34 is then controlled a signal, corresponding to the oxygen content, from a pipe or a tube 34b. A computer unit 35 with a memory 36 is mainly devised for internal unit functions.

There is nothing to prevent the modular unit 30 from containing e.g. a module and/or function-identification circuit 31 a devised to activate software stored in the basic unit 102.

There is nothing to prevent the replacement of a sensing circuit or a sensor 34 with a unit with activating means, such as magnetic valves.

Within the scope of the present invention, it is therefore possible to create conditions for measuring and monitoring a creature's diagnostic criteria and/or controlling the creature's therapeutic criteria.

Modular units including one or more therapeutic unit(s) and/or one or more diagnostic unit(s) can be advantageously arrayed on one or more board(s) with printed circuitry.

When software for all functions and criteria is installed in the basic unit 102, the said function-related software can be updated with or without a modular unit 30 installed in the basic unit 102.

As an alternative, a modular unit can be devised with hardware and/or software related to a single function.

A modular unit can be devised with hardware and/or some of the software related to a plurality of selected functions.

There is nothing to keep a selected number of modular units from being devised with hardware and/or software related to a single function.

Thus, one or more modular unit(s), co-acting with the said basic unit, will be able to offer sensing and/or processing of one and/or control of one or more function-related criterion/criteria.

The said criteria are related to one or more modular unit(s).

The said computer unit-related functions consist of sensing and/or processing and/or control of one or more of the following criterion/criteria, e.g.:

a) Oxygen measurement employing paramagnetic sensing ($600a'$).
b) Oxygen measurement employing chemical cell sensing ($600b'$).
c) Carbon dioxide measurement ($600c'$).
d) Pulse oximetry ($600d'$).
e) ECG ($600e'$).
f) Bi-spectral index ($600f'$).
g) Pressure, flow and/or volume in a unit ($600g'$).
h) NIBP value (blood pressure measured with a cuff). (See FIG. 1 and unit G) ($600h'$).
i) IBP value (blood pressure measured with a cannula in a blood vessel) ($600i'$).
j) Temperature measurement (the patient's) ($600j'$).
k) Cardiac output (measurement of the heart's minute volume) ($600k'$).
l) Lung ventilator, simple type ($600l'$).
m) Lung ventilator, advanced type ($600m'$).
n) Lung ventilator, high-frequency type ($600n'$).
o) Blood occlusion regulator ($600o'$).
p) Oxygen administration ($600p'$).
q) Infusion units of different kinds ($600q'$).
r) Nitrous oxide administration ($600r'$).

Figure 2:
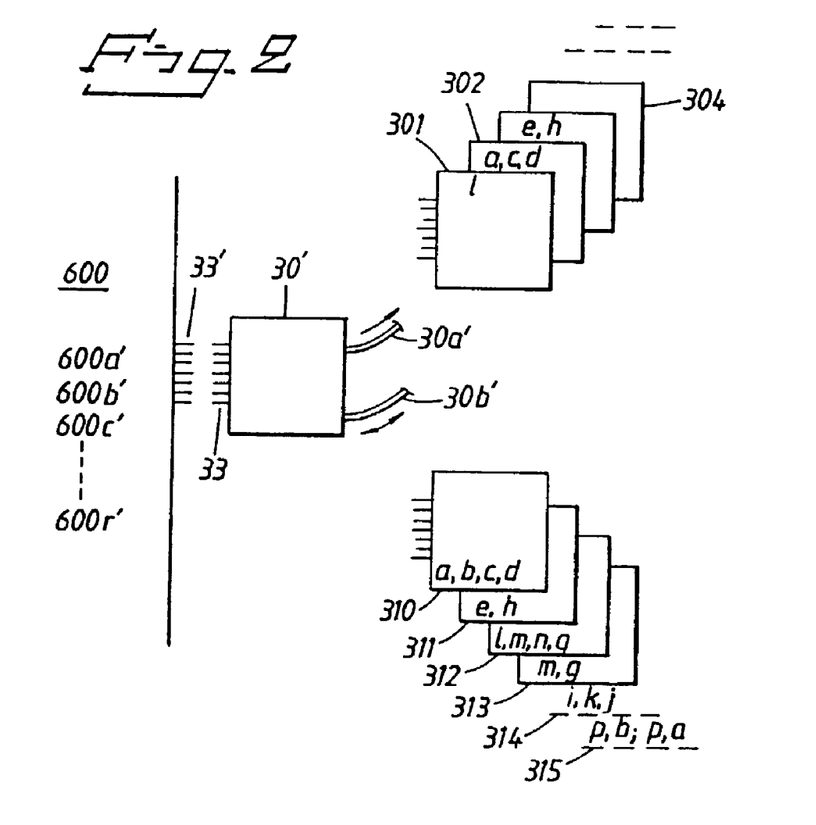
FIG. 2 is a schematic view of different applications and possible combinations for the invention.

Thus, FIG. 2 shows that a modular unit 310 can be devised to activate and/or control the computer unit-related functions listed under a, b and c and d above.

A second modular unit 311 shall be able to activate and control the functions under e and h.

A third modular unit 312 shall be able to activate and control the functions under l, m or n, preferably l and g. A fourth modular unit 313 can control the functions m and g.

An additional modular unit 314 can activate the functions under l, k and j, and a modular unit 315 can activate the functions under p and b. or under p and a.

The modular unit 30 contact 33 is devised to connect with the basic unit contact 33'.

Each of the modular units shall have one or more connecting line(s) to the creature. Only electrical lines are involved for certain modular units, a tube or tubes for others and both electrical lines and tubes for still others.

One modular unit 30' is devised for a lung ventilator and normally requires an input tube 30a' and an outlet tube.

One modular unit 30' devised for lung ventilation normally requires an outlet tube 30a' for insufflation gas and a duplex tube 30b' for control pressure to an expiratory valve (not shown).

However, this module 30' can be advantageously supplemented with pressure-flow-volume measurement, thereby requiring the use of an additional input tube for pressure measurement and two input tubes for differential pressure measurement.

The modular units can comprise therapeutic and/or diagnostic units with different functions in which criteria c and d are important.

Figure 5:
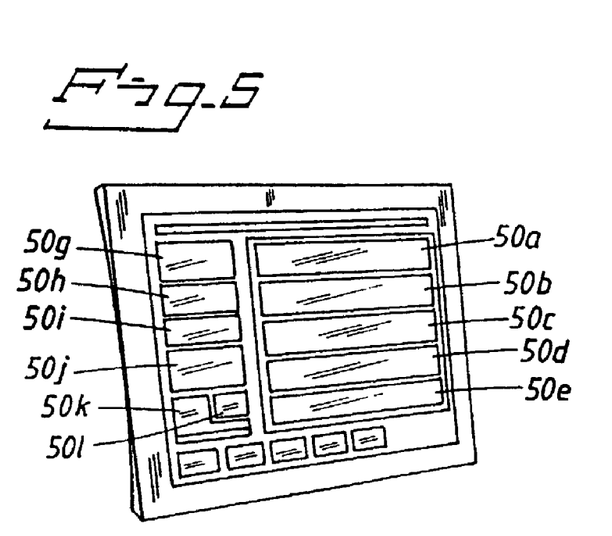
FIG. 5 shows a view of a display with a selective field subdivision for a second embodiment with the said two selected modular units supplemented with an additional modular unit.

A display unit is mounted on the basic unit. The display unit's display 50 is subdivided into a number of fields as shown in FIG. 4 or 5.

The purpose of the fields 50a, 50b, 50c, 50d and 50e is to indicate chronological variations in selected criteria.

FIG. 4 illustrates the invention with two modular units 30', 30. The modular unit 30' can be assumed to be for a lung ventilator (1), whereas the modular unit 30 can be assumed to be for oxygen measurement (a), carbon dioxide measurement (c) and pulse oximetry measurement (d) for determination of the $SpO_2$ value. The modular unit 30' must then have an input tube 34b and a line 34a.

FIG. 4 shows that the chronological variation in $CO_2$ and Plet values in this application can be displayed in segments 50b and 50c, $EtCO_2$-RR values are displayed in segment 50h, and $SpO_2$ and $FiO_2$ values are displayed in segment 50i.

If the array in FIG. 4 is supplemented with a module 30", devised for ECG and NIBP values, the display can show, according to FIG. 5, chronological variation for ECG in segment 50a, $CO_2$ in segment 50b and Plet values in segment 50c.

For NIBP and HR values, momentary values or averaged values can be displayed in segment 50g and otherwise according to FIG. 4.

FIG. 2 generally illustrates that the insertion of modular unit into a basic unit 102 causes the basic unit 102 to evaluate and control selected criteria $600a'$–$600r'$ stored therein.

The basic unit can be adapted for measurement and/or monitoring for modular units with a diagnostic unit and determination of diagnostic criteria.

The basic unit 102 can emit control signals for regulating different criteria via one or more selected modular unit(s) for modular units with a therapeutic unit and determination of therapeutic criteria.

The modular unit and basic unit can also be devised for duplex electrical communications.

FIG. 2 shows that only one modular unit 30', a lung ventilation unit, is electrically connected to the basic unit contact 33' via the contact 33.

This illustrates the use of an output tube 30a' for insufflation gas and an input and an output tube 30b' for generating a control pressure to an expiratory valve.

It is also proposed that a number of modular units 301–304 in FIG. 2 can each comprise a criteria-related unit or a selected combination of units.

Additional, previously described modular units 310–313 are devised for different combinations of criteria-related units.

It will be understood that the invention is not restricted to the aforesaid exemplifying embodiment and that modifications are possible within the scope of the inventive concept as defined in the following claims.

The invention claimed is:

1. An arrangement for inducing a state of anesthesia in a living creature and maintaining that creature in the state by intravenously administering to the creature a quantity and/or volume of anesthesia-inducing medication, comprising:
   a basic unit having a basic unit contact and a basic unit housing including a housing recess configured to simultaneously receive multiple modular units therein; and
   one of said modular units being attachable in parallel with respect to another modular unit within the housing recess and electrically connectable to the basic unit via said basic unit contact, said modular units being insertable into the housing recess via the basic unit contact and detachable therefrom, at least one of the modular units being configured to cooperate with the basic unit to activate one or more functions stored in the basic unit as computer software, said one or more functions being related to anesthetizing a creature, and at least one of the modular units being configured to measure and/or monitor the diagnostic criteria of the creature or control the therapeutic criteria of the creature;
   wherein at least one modular unit contains a processor connected to a system identification circuit with a selected electronic interface, and a function-related sensor operatively connected to the system identification circuit; and wherein the least one modular unit contains a module-identification and/or function-identification circuit with the system identification circuit; the module-identification circuit and/or function-identification circuit being configured to activate computer software stored in the basic unit; and wherein at least one of the modular units is configured with hardware and/or software related to a plurality of selected functions.

2. An arrangement according to claim 1, wherein said modular units include a unit for sensing diagnostic criteria.

3. An arrangement according to claim 2, wherein said unit for sensing diagnostic criteria, comprises one or more computer units.

4. An arrangement according to claim 1, wherein said modular units include a unit capable of affecting therapeutic criteria.

5. An arrangement according to claim 4, wherein said unit capable of affecting therapeutic criteria comprises one or more computer unit.

6. An arrangement according to claim 1, wherein at least one of said modular units cooperate with the basic unit in order to achieve selected basic unit functions, and wherein software is distributed between the basic unit and one or more modular unit.

7. An arrangement according to claim 1, wherein at least one of said modular units comprises function-related hardware, related to one or more criteria.

8. An arrangement according to claim 1, wherein said function-related computer software, is configured for operating with said diagnostic or therapeutic criteria.

9. An arrangement, according to claim 8, wherein said function-related software stored in the basic unit can be updated without the modular unit initiating the update.

10. An arrangement according to claim 1, wherein at least one of said modular units is configured with hardware and/or software related to a single function.

11. An arrangement according to claim 1, wherein at least one of said modular units is configured with hardware and/or software related to a plurality of selected functions.

12. An arrangement according to claim 1, wherein a plurality of said modular units is configured with hardware and/or software related to a single function.

13. An arrangement according to claim 1, wherein at least one of said modular units cooperates with said basic unit to provide sensing of one or more function-related criteria.

14. An arrangement according to claim 1, wherein function-related software stored in the basic unit is configured for making a distinction between therapeutic criteria and diagnostic criteria when therapeutic modular units and/or diagnostic modular units are attached to the basic unit.

15. An arrangement according to claim 1, wherein one or more first criteria, related to one or more diagnostic units, and one or more second criteria, related to one or more therapeutic units, can be displayed on a screen, one or more of said first criteria are selected for screen display as momentary values, and one or more of said first criteria are selected for screen display of chronological variations in the criterion.

16. An arrangement according to claim 15, wherein one or more of said second criteria are selected for screen display as momentary values, and one or more of said second criteria are selected for screen display of chronological variation in the criterion.

17. An arrangement according to claim 15, wherein time axes for certain criteria, selected for display as the criterion's chronological variation are coordinated and stacked atop one another.

18. An arrangement according to claim 15, wherein a sensor signals for some criteria are delayed.

19. An arrangement according to claim 15, momentary values for one or more criteria related to one or more diagnostic units, and/or momentary values for one or more criteria related to one or more therapeutic units, can be stored in memories for display, when needed, as the criterion's chronological variation.

20. An arrangement according to claim 15, wherein said momentary values can be stored time-related in memories so chronological curves can be displayed, thereby reproducing a curve's trend, or alternately displaying variations in a compressed time format.

21. An arrangement according to claim 1, wherein said basic unit housing has a front, and said housing recess is in said front of said basic unit housing.

22. An arrangement for inducing a state of anesthesia in a living creature and maintaining that creature in the state by intravenously administering to said creature a quantity and/or volume of anesthesia-inducing medication, comprising:

a basic unit comprising a basic unit housing including a housing recess configured to simultaneously receive multiple modular units therein, a basic unit contact, and one or more modular units being insertable in said recess of the basic unit housing via the basic unit contact and detachable therefrom; and one of said modular units being attachable in parallel with respect to another modular unit and electrically connectable to the basic unit via said basic unit contact, at least one of the modular units being configured to cooperate with the basic unit to activate one or more functions stored in the basic unit as computer software, said one or more functions being related to anesthetizing a creature, wherein at least one modular unit contains a processor connected to a system identification circuit with a selected electronic interface, and a function-related sensor operatively connected to the system identification circuit; and wherein the least one modular unit contains a module-identification and/or function-identification circuit with the system identification circuit; the module-identification circuit and/or function-identification circuit being configured to activate computer software stored in the basic unit; and wherein at least one of the modular units is configured with hardware and/or software related to a plurality of selected functions.

and at least one of the modular units being configured to measure and/or monitor the diagnostic criteria of the creature or control the therapeutic criteria of the creature, at least one of said modular units being configured to cooperate with said basic unit to provide sensing of one or more function-related criteria, said function-related criteria being:

a) Oxygen measurement employing paramagnetic sensing;
b) Oxygen measurement employing chemical cells;
c) Carbon dioxide measurement;
d) Pulse oximetry;
e) EGG;
f) Bi-spectral index;
g) Pressure, flow and/or volume in one unit;
h) NIBP value (blood pressure measured with a cuff);
i) IBP (blood pressure measured with a cannula in a blood vessel);
j) Measurement of patient temperature;
k) Cardiac output (measurement of the heart's minute volume);
l) Lung ventilator, simple type;
m) Lung ventilator, advanced type;
n) Lung ventilator, high frequency type;
o) Blood occlusion regulator;
p) Oxygen administration;
q) Infusion units of various kinds; and
r) Nitrous oxide administration.

23. An arrangement according to claim 22, wherein a modular unit is configured for activating and/or controlling functions associated with the paramagnetic sensing or chemical cells oxygen measurement criteria and carbon dioxide measurement criteria or pulse oximetry criteria.

24. An arrangement according to claim 22, wherein one of said modular units is configured for activating and/or controlling functions associated with EGG criteria and NIBP value criteria.

25. An arrangement according to claim 22, wherein one of said modular units is configured for activating and/or controlling functions associated with a simple or high frequency type lung ventilator, or a simple type lung ventilator and a unit for measuring pressure, flow and/or volume in one unit.

26. An arrangement according to claim 22, wherein one of said modular units is configured for activating and/or controlling functions associated with an advanced type lung ventilator and a unit for measuring pressure, flow and/or volume in one unit.

27. An arrangement according to claim 22, wherein one of said modular units is configured for activating and/or controlling functions associated with a simple type lung ventilator, a device for measuring cardiac output and a device for measuring patient temperature.

28. An arrangement according to claim 22, wherein one of said modular units is configured for activating and/or controlling functions associated with oxygen administration and paramagnetic sensing or chemical cells oxygen measurement criteria.

29. An arrangement according to claim 22, wherein said basic unit housing has a front, and said housing recess is in said front of said basic unit housing.

* * * * *

UNITED STATES PATENT AND TRADEMARK OFFICE
CERTIFICATE OF CORRECTION

PATENT NO. : 7,044,930 B2
APPLICATION NO. : 10/181491
DATED : May 16, 2006
INVENTOR(S) : Stefan Per Axel Stromberg It is certified that error appears in the above-identified patent and that said Letters Patent is hereby corrected as shown below:

In Column 15, Claim 22, Lines 30-31:
    Please replace "functions." with --functions,--

Signed and Sealed this

Seventh Day of November, 2006

JON W. DUDAS
*Director of the United States Patent and Trademark Office*